United States Patent
Whalen

(10) Patent No.: US 7,507,585 B2
(45) Date of Patent: Mar. 24, 2009

(54) METHODS AND SYSTEMS FOR INDENTIFYING AND MONITORING S-NITROSOTHIOLS IN BIOLOGICAL SAMPLES

(76) Inventor: Erin J. Whalen, 4408 Regis Ave., Durham, NC (US) 27705

( * ) Notice: Subject to any disclaimer, the term of this patent is extended or adjusted under 35 U.S.C. 154(b) by 591 days.

(21) Appl. No.: 11/032,400

(22) Filed: Jan. 10, 2005

(65) Prior Publication Data

US 2006/0154376 A1 Jul. 13, 2006

(51) Int. Cl.
G01N 33/50 (2006.01)
G01N 33/487 (2006.01)
(52) U.S. Cl. .................. 436/120; 435/188; 435/7.5; 435/375
(58) Field of Classification Search .................. 435/188, 435/7.5, 375; 204/180.1
See application file for complete search history.

(56) References Cited

U.S. PATENT DOCUMENTS

| | | | |
|---|---|---|---|
| 5,063,151 | A | 11/1991 | Kuehn et al. |
| 5,346,599 | A | 9/1994 | Stamler et al. |
| 5,538,856 | A | 7/1996 | Levy et al. |
| 5,618,664 | A | 4/1997 | Kiessling |
| 6,605,447 | B2 | 8/2003 | Weiss et al. |
| 6,806,057 | B2 | 10/2004 | Snyder et al. |
| 2002/0102744 | A1* | 8/2002 | Snyder et al. ............... 436/538 |
| 2004/0067595 | A1 | 4/2004 | Davies et al. |
| 2004/0235163 | A1* | 11/2004 | Yokota ....................... 435/375 |

FOREIGN PATENT DOCUMENTS

WO   WO 02/16934   *  2/2002

OTHER PUBLICATIONS

Schmidt, et al., "$Ca^{2+}$/Calmodulin-Dependent NO Synthase Type I: A Biopteroflavoprotein with $Ca^{2+}$/Calmodulin-Independent Diaphorase and Reductase Activities," *Biochemistry*, vol. 31, pp. 3243-3249, 1992.
Dawson, et al., "Nitric Oxide Synthase and Neuronal NADPH Diaphorase are Identical in Brain and Peripheral Tissues," *Proc. Natl. Acad. Sci. USA*, vol. 88, pp. 7797-7801, Sep. 1991.
Hope, et al., "Neuronal NADPH Diaphorase is a Nitric Oxide Synthase," *Proc. Natl. Acad. Sci. USA*, vol. 88, pp. 2811-2814, Apr. 1991.
Gergel, et al., "Interaction of Nitric Oxicde with 2-Thio-5-nitrobenzoic Acid: Implications for the Determination of Free Sulfhydryl Groups by Ellman's Reagent," *Archives of Biochemistry and Biophysics*, vol. 347, No. 2, pp. 282-288, Nov. 1997.
Gow, et al., "A Novel Reaction Mechanism for the Formation ofS-Nitrosothiol in Vivo," *The Journal of Biological Chemistry*, vol. 272, No. 5, pp. 2841-2845, Jan. 31, 1997.
Samouilov, et al., "Development of Chemiluminescence-Based Methods for Specific Quantitation of Nitrosylated Thiols," *Analytical Biochemistry*, vol. 258, pp. 322-330, 1998.

Aimar, et al., "Nitric Oxide-Producing Islet Cells Modulate the Release of Sensory Neuropeptides in the Rat Substantia Gelatinosa," *The Journal of Neuroscience*, vol. 18, No. 24, pp. 10375-10388, Dec. 15, 1998.
Gaston, et al., "Umbilical Arterial S-nitrosothiols in Stressed Newborns: Role in Perinatal Circulatory Transition,"*Biochemical and Biophysical Research Communications*, vol. 253, pp. 899-901, 1998.
Gow, et al., "The Oxyhemoglobin Reaction of Nitric Oxide," *Proc. Natl. Acad. Sci. USA*, vol. 96, pp. 9027-9032, Aug. 1999.
Babior, Bernard M., "NADPH Oxidase: An Update,"*Blood*, vol. 93, No. 5, pp. 1464-1476, Mar. 1, 1999.
Gagioti, et al., "Participation of the Mouse Implanting Trophoblast in Nitric Oxide Production During Pregnancy," *Biology of Reproduction*, vol. 62, pp. 260-268, 2000.
Lau, et al., "Arginine, Citrulline, and Nitric Oxide Metabolism in End-Stage Renal Disease Patients," *The Journal of Clinical Investigation*, vol. 105, No. 9, pp. 1217-1225, 2000.
Van Der Vliet, et al., "Nitric Oxide: A Pro-inflammatory Mediator in Lung Disease," *Respir Res*, vol. 1, pp. 67-72, 2000.
Jourd'Heuil, et al., "S-Nitrosothiol Formation in Blood of Lipopolysaccharide-Treated Rats," *Biochemical and Biophysical Research Communications*, vol. 273, pp. 22-26, 2000.
Tyurin, et al., "Elevated Levels of S-Nitrosoalbumin in Preeclampsia Plasma," *Circulation Research*, vol. 88, pp. 1210-1215, Jun. 8, 2001.
Ottesen, et al., "Increased Formation of S-Nitrothiols and Nitrotyrosine in Cirrhotic Rats During EndoToxemia," *Free Radical Biology & Medicine*, vol. 31, No. 6, pp. 790-798, 2001.
Marley, et al., "Formation of Nanomolar Concentrations of S-Nitrosoalbumin in Human Plasma By Nitric Oxide," *Free Radical Biology & Medicine*, vol. 21, No. 5, pp. 688-696, 2001.
Crane, et al., "Novel Role for Low Molecular Weight Plasma Thiols in Nitric Oxide-mediated Control of Platelet Function,"*The Journal of Biological Chemistry*, vol. 277, No. 49, pp. 46858-46863, Dec. 6, 2002.
Wlodek, et al., "Alteration in Plasma Levels of Nonprotein Sulfhydryl Compunds andS-Nitrosothiols in Chronic Renal Failure Patients," *Clinica Chimica Acta*, vol. 327, pp. 87-94, 2003.
Vogt, et al., "The Metabolism of Nitrosothiols in the Mycobacteria: Identification and Characterization of S-nitrosomycothiol Reductase," *Biochem. J.*, vol. 374, pp. 657-666, 2003.
Ott, et al., "New Techniques for Whole-mount NADPH-diaphorase Histochemistry Demonstrated in Insect Ganglia," *The Journal of Histochemistry & Cytochemistry*, vol. 51, No. 4, pp. 523-532, 2003.

(Continued)

*Primary Examiner*—Walter D Griffin
*Assistant Examiner*—Christine T Mui
(74) *Attorney, Agent, or Firm*—Marianne Fuierer; Moore & Van Allen PLLC

(57) ABSTRACT

The present invention describes methods and kits for determining the level of S-nitrosothiols in biological fluid samples. The method includes separating tissue or cellular matter from the biological fluid sample and then contacting the biological fluid sample with paraformaldehyde in an amount sufficient to fix free thiols thereby essentially eliminating diaphorase activity of the free thiols. The biological fluid sample is then contacted with NADPH and nitro blue tetrazolium (NBT) wherein S-nitrosothiols in the biological fluid sample facilitate the reduction of NBT to NBT formazan or diformazan in the presence of paraformaldehyde. The amount of reduced NBT is measured and the determined levels correlate to the amount of S-nitrosothiols in the biological fluid sample.

22 Claims, No Drawings

OTHER PUBLICATIONS

Yang, et al., "Methodologies for the Sensitive and Specific Measurement of S-nitrosothiols, Iron-nitrosyls, and Nitrite in Biological Samples," *Free Radical Research*, vol. 37, pp. 1-10, 2003.

Stamler, Jonathan S., "S-Nitrosothiols in the Blood," *Circulation Research*, vol. 94, pp. 414-417, Mar. 5, 2004.

Ishibashi, et al., "New Methods to Evaluate Endothelial Function: A Search for a Marker of Nitric Oxide (NO) in Vivo: Re-evaluation of NOx in Plasma and Red Blood Cells and a Trial to Detect Nitrosothiols," *J. Pharmacol. Sci.*, vol. 93, pp. 409-416, 2003.

Massy, et al., "Increased Plasma S-Nitrosothiol Levels in Chronic Haemodialysis Patients," *Nephrol Dial Transplant*, vol. 18, pp. 153-157, 2003.

Liu, et al., "Essential Roles of S-Nitrosothiols in Vascular Homeostasis and Endotoxic Shock," *Cell*, vol. 116, pp. 617-628, Feb. 20, 2004.

Massy, et al., "Increased Plasma S-Nitrosothiol Concentrations Predict Cardiovascular Outcomes Among Patients with End-Stage Renal Disease: A Prospective Study," *J. Am. Soc. Nephrol.*, vol. 15, pp. 470-476, 2004.

Palmerini, et al., "Electrochemical Assay for Determining Nitrosyl Derivatives of Human Hemoglobin: Nitrosylhemoglobin and S-Nitrosylhemoglobin," *Analytical Biochemistry*, vol. 330, pp. 306-310, 2004.

Giustarini, et al., "Nitric Oxide: S-Nitrosothiols and Hemoglobin: Is Methodology the Key?" *TRENDS in Pharmacological Sciences*, vol. 25, No. 6, pp. 312-315, Jun. 2004.

Beckman, Joseph S., The physiological and pathological chemistry of nitric oxide. In: Nitric Oxide: Principles and Actions (ed. J Lancaster) Academic Press, NY, pp. 1-82, 1996.

Tsikas, D., et al., "Are plasma S-nitrosothiol Levels elevated in chronic renal failure?" *Nephrol Dial. Transplant*, 1 vol. 8., pp. 2199-2201, 2003.

Tsikas, D., "S-Nitrosoalbumin and other S-nitrosothiols in the blood-Is their quantity of no relevance?" Circulation Research, vol. 94 (12), pp. E106-E106, 2004.

Lewis, et al., S-Nitrosothiols Augment Electron-Transfer from NAD(P)H to Nitroblue Tetrazolium., FASEB Journal, vol. 8 (5), A595., 1994.

S.J. Lewis et al.; S-Nitrosothiols Augment Electron Transfer from NAD(P)H to Nitroblue Tetrazolium; (SPON: A.K. Johnson), Depts. of Pharmacology, Anesthesia and the Cardiovascular Center, University of Iowa, Iowa City, IA; USA (Abstract Only).

* cited by examiner

METHODS AND SYSTEMS FOR INDENTIFYING AND MONITORING S-NITROSOTHIOLS IN BIOLOGICAL SAMPLES

BACKGROUND OF THE INVENTION

1. Technical Field

The present invention relates generally to biological assays, and more particularly to a method and system for identifying and monitoring nitrosothiol moieties in fluidized biological samples.

2. Description of Related Art

Nitric oxide (NO) is a molecule, which is biologically important in both a physiological and a pathological sense and implicated in biological processes, including control of systemic blood pressure, respiration, digestion, platelet aggregation and cerebral blood flow, as well as contributing to the microbicidal and tumouricidal activities of macrophages. Nitric oxide is an endogenous bioactive molecule produced by the conversion of L-arginine to L-citrulline by the nitric oxide synthase (NOS) family of enzymes.

Under physiological conditions, NO is unstable and easily reacts with oxygen to form oxides of nitrogen (NOx). Thus, it is difficult to measure levels of nitric oxide because it exists as a free radical with a short half-life of approximately 10 to 30 seconds in aqueous solution and approximately 0.46 ms in whole blood (Feelisch, M, Stampler, J. S., Methods in Nitric Oxide Research, John Wiley & Sons, New York, 1st Edition 49-65 (1996)). Consequently, many of the reports implicating NO in various physiological processes and many disease states are based on the measurement of NO metabolites or NO containing compounds. These NO containing compounds include S-nitrosothiols that are known to be formed in vivo by S-nitrosation of thiol-containing proteins and peptides, such as albumin and hemoglobin, as well as smaller molecular weight compounds such as cysteine, glutathione, homocysteine, etc.

S-nitrosothiols are endogenous biologically active nitric oxide containing compounds in which nitric oxide in the form of nitrosonium ion, NO+, is attached to the free sulfhydryl group of a cysteine residue. S-nitrosothiols exist as both small (S-nitrosocysteine, S-nitrosoglutathione, etc.) and large (such as S-nitrosoalbumin, nitrosylated proteins, etc.) molecular weight compounds and can be found at various levels throughout the body where they are capable of initiating signaling processes similar to as well as distinct from those associated with the NO radical.

Recent studies suggest that alterations in biological S-nitrosothiol levels are linked to asthma, inflammation, hypertension, apoptosis and atherosclerosis and are predictive of adverse outcomes. For example, Corradi et al. (*American Journal of Respiratory and Critical Care Medicine*, "Increased Nitrosothiols in Exhaled Breath Condensate in Inflammatory Airway Disease" V. 163: pp. 854-858 (2001) found that S-nitrosothiol levels increased in patients with severe asthma; Tyurin et al., (*Circulation Research*, "Elevated Levels of S-Nitrosoalbumin in Preeclampsia Plasma" V. 88: p. 1210, (2001)) determined that plasma concentration of S-nitrosothiols was much higher in women with preeclampsia then women experiencing a normal pregnancy; and Massey, et al. (*J. Am. Soc. Nephrol.*, "Increase Plasma S-Nitrosothiol Concentration Predict Cardiovascular Outcomes among Patients with End-Stage Renal Disease" V. 15: pp. 470-476 (2004)) determined that levels of S-nitrosothiols, are increased among patient undergoing chronic hemodialysis and this high level seems to be due to reduced breakdown of the S-nitrosothiols which causes less bioavailability of the molecule to the patient and contributes to increased negative cardiovascular events.

Therefore, with the increased levels of nitrosothiols shown to correlate with multiple disease states, the ability to functionally assess these levels in biological fluids represents a valuable tool for aiding in the diagnosis and treatment of disease. At present, there exist several methods for assaying nitrosothiol levels in biological fluid samples. The most popular is the Saville assay that is based on mercury ion-mediated heterolytic cleavage of the S—NO bond. Other methods include uv/visible spectroscopy, fluorescence spectroscopy, and the high performance liquid chromatography (HPLC) analysis, which can be combined with chemiluminescence or an electrochemical detector. However, these assays are limited in their current clinical application by overly complex methodologies, cost-ineffective material requirements, insufficient sensitivity and low throughput and/or assay duration.

Therefore, there exists a need for a clinically applicable assay to determine the level of S-nitrosothiols that uses a simple methodology that is convenient, scalable, cost effective, and reproducible with sufficient specificity and sensitivity to accurately measure the level of nitrosothiol in fluidized samples without unwanted artifacts.

SUMMARY OF THE INVENTION

The present invention relates to a method of assaying S-nitrosothiols which is quantitative and which is sufficiently sensitive to be used in biological fluid samples.

In one aspect the present invention provides a method for screening a biological fluid sample for S-nitrosothiols, the method comprising:

(a) contacting the biological fluid sample with a fixation agent in an amount sufficient to bind or block free thiols in the biological fluid sample thereby essentially eliminating diaphorase activity of said free thiols and wherein the fixation agent does not reduce the diaphorase activity of any S-nitrosothiols in the sample;

(b) contacting the biological fluid sample with at least one redox indicator, wherein the S-nitrosothiols in the biological fluid sample facilitate the reduction of the redox indicator in the presence of the fixative solution, (c) measuring the level of reduction of the redox indicator thereby quantifying the amount of S-nitrosothiols in the biological fluid sample.

The biological sample may further comprise introducing an electron donor component at approximately the same time as the redox indicator is added to the sample. Preferably, the electron donor is NADPH or a functional equivalent thereof.

In another aspect the present invention provides for a method for screening a biological fluid for endogenous and/or inducible S-nitrosothiols, the method comprising:

(a) separating essentially all tissue or cellular matter from the biological fluid sample;

(b) contacting the biological fluid sample with paraformaldehyde in an amount sufficient to fix free thiols in the biological fluid sample thereby essentially eliminating diaphorase activity of the free thiols;

(c) contacting the biological fluid sample with nitro blue tetrazolium (NBT) or a functional derivative thereof wherein S-nitrosothiols in the biological fluid sample facilitate the reduction of NBT to NBT formazan or diformazan in the presence of paraformaldehyde; and (d) spectrophotometrically detecting the level of NBT formazan or diformazan thereby quantifying the amount of S-nitrosothiols in the biological fluid sample.

The invention further relates to a method for monitoring the extent of a disease state involving abnormal levels of S-nitrosothiols in biological fluids of a patient, the method comprising:
(a) contacting a biological fluid sample with paraformaldehyde in an amount sufficient to fix free thiols in the biological fluid sample thereby essentially eliminating diaphorase activity of the free thiols;
(b) contacting the biological fluid sample with NADPH and nitro blue tetrazolium (NBT) wherein S-nitrosothiols in the biological fluid sample facilitate the reduction of NBT to NBT formazan or diformazan in the presence of paraformaldehyde; and
(c) measuring the level of reduced NBT thereby quantifying the amount of S-nitrosothiols in the biological fluid sample.

In particular, said disease state may be selected from the group comprising septic shock, cardiogenic shock, hypovolemic shock, atherosclerosis, hyperhomocysteinemia, venus thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infection and central nervous system disorders, renal disease, cardiovascular disease, asthma, rheumatoid arthritis, tuberculosis, diabetes, inflammatory joint diseases, cerebral ischaemia, preeclampsia, brain injury, hypertension, cardiac hypertrophy, ocular injury and infection, and many others.

The present invention also relates to methods wherein the biological fluid sample is selected from the group comprising urine, blood, tears, plasma, serum, cerebrospinal fluid, semen, synovial fluid, peritoneal fluid, intestinal secretions, sputum, stool, saliva, mucus, corneal fluid, amniotic fluid, bile, lymph, vaginal secretions, tumor fluid, perspiration or others.

In yet another aspect, the present invention relates to a method for detecting, diagnosing or monitoring the progress of a disease in a patient, the method comprising steps:
(a) obtaining a fluid sample of blood, plasma, serum, urine or saliva from the a patient;
(b) subjecting said sample to a procedure for detecting S-nitrosothiols in the fluid sample; and
(c) detecting, diagnosing or monitoring the course of the disease by comparing levels of S-nitrosothiols obtained from the patient to levels obtained from a control sample or earlier sample from the patient.

Another aspect of the invention relates to a method of evaluating the efficacy or toxicity of a drug therapy which modulates S-nitrosothiol levels, the method comprising:
(a) treating a sample of fluidized biological sample with paraformaldehyde in an amount sufficient to fix free thiols and inactivate activity of enzymes in the fluidized biological sample thereby essentially eliminating diaphorase activity of the free thiols and enzymes;
(b) treating the fluidized biological sample with a testing compound and nitro blue tetrazolium (NBT) wherein S-nitrosothiols in the fluidized biological sample facilitates the reduction of NBT to NBT formazan or diformazan in the presence of paraformaldehyde; and
(c) measuring the level of NBT formazan or diformazan thereby quantifying the amount of S-nitrosothiol in the fluidized biological sample and comparing the level of S-nitrosothiols relative to a fluidized biological sample untreated with the testing compound.

This method is advantageously used to determine if a specific drug therapy or environmental pathogen/contaminant exposure modulates levels of NO, S-nitrosothiols, NO donor, NO-releasing pro-drug, nitrosothiol forming pro-drug (i.e. ethyl nitrite), direct/indirect NOS activator, NOS inhibitor, NO scavenger or S-nitrosothiol scavenger.

The biological sample may further comprise the introduction of NADPH at approximately the same time the redox indicator NBT is added to the sample.

A method for detecting the amount of S-nitrosothiols in a biological fluid sample, said detection comprising the steps of:
(a) contacting the biological fluid sample with paraformaldehyde in an amount sufficient to fix free thiols in the biological fluid sample thereby essentially eliminating diaphorase activity of the free thiols;
(b) contacting the biological fluid sample with NADPH and nitro blue tetrazolium wherein S-nitrosothiols in the biological fluid sample facilitate the reduction of NBT to NBT formazan or diformazan in the presence of paraformaldehyde; and
(c) quantitating the amount of S-nitrosothiols in the sample by measuring the absorption signal generated by the concentration of reduced NBT.

Still yet another aspect of the present invention is a kit for detecting levels of nitrosothiols in fluidized biological samples such as saliva, blood, plasma, serum or urine. Generally, the kits for detection of nitrosothiols in fluidized biological samples may include 1) a filtering system for filtering the fluidized biological sample to separate essentially all tissue or cellular matter; and 2) at least one container comprising a fixation agent in a sufficient amount to fix free thiols in the fluidized biological sample, and a redox indicator in an amount sufficient to react with any nitrosothiol moieties in the fluidized biological sample. Preferably, the filtering system is in fluid communication with the container and included as a single separatable unit.

Further, applicable kits for detection of S-nitrosothiols may comprise a container including a solid support having immobilized thereon the fixation agent for flowing the fluidized biological sample therethrough. Preferably, any kit system will further include a filtering system for initial filtering of the biological fluid to remove essentially all tissue remnants. Various kits and assay systems that can be easily modified for practicing the current invention are known in the art and it will be apparent to any person skilled in the art how to use this invention for its intended purpose.

Other aspects and features of the invention will be more fully apparent from the ensuing disclosure and appended claims.

DETAILED DESCRIPTION OF THE INVENTION

In a general aspect, the present invention describes methods and kits for determining the level of endogenous and induced S-nitrosothiol levels in fluidized biological samples. Further, the methods of the present invention do not use photolytic-chemiluminescence or spin-trap resonance, thereby greatly simplifying the assay and expanding its applicability for measuring the levels of S-nitrosothiols whether generated in vitro or in vivo.

The term "S-nitrosothiols," as used herein, means a group of organic sulfur containing nitrites, alkyl thionitrites, including S-nitroso-N-acetylpenicillamine, S-nitrosoglutathione, S-nitrosocysteine, 5-nitrosoalbumin, nitrosylated proteins, S-nitroso-N-acetyl cysteine, S-nitrosohomocysteine, S-nitros coenzyme A, etc.

The terms "fixation agent or fixing agent," as used herein, means an agent that interacts with free thiols by blocking, binding, fixing or modifying any free thiols in the fluidized biological sample thereby removing the free thiols or inhibiting same from contributing to the results of the assay.

The terms "fixing," "binding," "blocking," and "modifying," as used herein relative to free thiols, are used interchangeably to mean interacting with the free thiols to removing or inhibit any diaphorase activity of the free thiols.

The term "functional derivative," as used herein, means a compound that includes new or different moieties not normally a part of the original compound but retains some or all of the functional and/or biological activity of the original compound.

The multi-step methods of the present invention employ a redox indicator, wherein S-nitrosothiols in the biological fluid sample facilitate the reduction of such a redox indicator. However, before introducing the redox indicator, it is particularly important to ensure that the assay is carried out under conditions that reduce erroneous results due to free thiols in the biological fluid. Thus, in one of the first steps, any free thiols in the sample are modified or blocked by fixation with at least one thio-capturing agent that reacts with any free thiol groups in the biological sample thereby modifying or blocking the free thiols and allowing for determination of other thiol containing compounds. Generally, any fixation agent may be used that interacts with or binds free thiols leaving stable disulfides intact, or reduces and then blocks preexisting disulphide bonds but does not interact with nitrosothiols. Preferably, the fixation agent includes, but is not limited to, paraformaldehyde, formaldehyde, maleimide, diamide, n-ethymaleimide, iodoacetate, iodoacetamide (disulphide thiols), 5',5'-dithio-bis-3-nitrobenzoate (DTNB), 4-(N-(S-glutathionylacetyl)amino)-phenylarsenoxide (GSAO), methyl methanethiolsulphonate (MMTS), 4,4' dithiodipyridine, monoisoamyl 2,3-dimercaptosuccinic acid (Mi-ADMSA), meso-2,3-dimercaptosuccinic acid (DMSA), tris-(2-carboxyethyl)phosphine (TCEP), tris-(2-cyanoethyl) phosphine, dansyl aziridine, acrylodan, 2-aminoethyl-2'-aminoethane thiosulfonate. More preferably, the fixation agent is paraformaldehyde.

Importantly, in the presence of paraformaldehyde or like compounds, which are capable of binding, chelating, oxidizing or further modifying the reduced free thiol of a cysteine residue, diaphorase activity is all but eliminated. Further, the enzymatic activity of nitric oxide synthase (NOS) is eliminated, and as such, any diaphorase activity determined in the fluidized sample can be attributed to S-nitrosothiol moieties. Importantly, this elimination of diaphorase activity by other components in the fluidized sample indicates that the paraformaldehyde does not need to be removed from the fluidized sample before proceeding to the next step, thereby advantageously reducing steps that are required to quantify S-nitrosothiols in the sample.

Previously it was demonstrated by Lewis et al., 1994, "S-Nitrosothiols Augment Electron-Transfer from NAD(P)H to Nitroblue Tetrazolium," *FASEB Journal;* 8 (5) p. A595, and Belasco et al. 1997, "Biochemical and Histochemical Characterization of Preformed Nitric Oxide (NO)-Containing Factors (NOFs) in Neurons and Vascular Endothelial Cells," FASEB Journal; 11 (1) p. 492, that S-nitrosothiols in contrast to free thiols, such as cysteine could also promote the NADPH dependent reduction of NBT in the presence of paraformaldehyde. However, it was not recognized by either Lewis, et al. or Belasco et al. that paraformaldehyde could be used with a fluidized biological sample for incorporation in an S-nitrosothiol assay.

The free thiol fixation agent can be added directly to the fluidized biological sample or in the alternative the fixation agent can be covalently or non-covalently immobilized on a solid support and the fluidized sample is passed through the column. The term "solid support" may be a purification column, a discontinuous phase of discrete particles, a membrane or filter. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above. In preferred embodiments, the solid support comprises controlled pore beads retained in a column that are coated with the fixation agent.

Use of a solid support provides for not only the fixation of free thiols in the biological solution but also the separation of different size S-nitrosothiols. Retaining larger proteins in a column allows for distinguishing between small molecular weight and larger molecular weight S-nitrosothiols. For example, small molecular weight S-nitrosothiols, such as S-nitrosocysteine, S-nitrosoglutathione and S-nitrosohomocysteine, contain only one nitrosylated thiol and no free thiols, and would therefore not be retained in a thiol capturing column, as described above. Further, larger molecular weight nitrosothiols such as S-nitrosoalbumin may in fact also contain a number of free thiols and would therefore be retained in the column. As such, methods of the present invention provide for determination of not only the total levels of S-nitrosothiols in a fluidized biological sample but also separation of different S-nitrosothiols having varied molecular weights that may have different biological significance relevant to a particular disease process.

The stability of S-nitrosothiols under physiological conditions is known to be dependent upon various factors including the nature of the thiol group (RS) to which the NO group is attached. Examples of RS molecules include glutathione, cysteine, albumin and hemoglobin. Other factors that affect the stability of S-nitrosothiols include pH, oxygen tension, redox state and the presence of trace amounts of transition metals. Thus, in the test methods of the present invention, fluidized biological samples, preferably also include additional components for controlling pH and/or complexing with trace metals in the sample.

The pH of the biological sample, during the assay method is preferably maintained at a pH that resists the breakdown of S-nitrosothiols or the precipitation of same. Accordingly, the pH is maintained in a near neutral range to prevent the instability of nitrosothiols that occurs under alkaline conditions or the precipitation of nitrosothiols that occurs under acidic conditions. Preferably, the pH is maintained in a range from about 6.5 to about 8.5. Notably, by increasing the pH of the sample when contacting with NBT can be used to increase the rate of the overall reaction.

In light of the fact that it is known that copper ions are often used to facilitate the breakdown of S-nitrosothiols to yield NO (Fang et al, *Biochem. Biophys. Res. Comm.,* 252(3), 535-540 (1998)), is important to include a metal chelating agent such as ethylene diamine tetraacetic acid (EDTA) or diethylenetriaminepentaacetic acid (DPTA), to form metal complexes thereby inhibiting any tendency for decomposition of S-nitrosothiols in the fluidized biological sample. Clearly, when the sample to be tested is a blood product, it is preferable to add a chelating agent such as (EDTA) to the sample upon or soon after collection in order to chelate excess transition metal ions that could react with S-nitrosothiols during sample preparation and storage.

Advantageously, the methods of the present invention can determine the concentration of S-nitrosothiols as low as $10^{-5}$ M or lower depending on the amount of sample available in human or animal blood, serum, plasma, synovial fluid, urine cerebrospinal fluid, peritoneal fluid, gingival crevicular fluid or any other tissue or extracellular fluid of human or animal origin. Alternatively, the concentration of S-nitrosothiols may be determined in other biological media, such as cell culture media, or in a chemical system.

Importantly, the biological sample is preferably in a clarified mode, meaning that essentially all cellular tissue or particular matter has been separated from the sample. Clarification can be effected by any separation means that will separate cellular tissue from the sample thereby providing a fluidized biological sample. The separation means may include centrifuge, column separation or ultra-fine filters used in conjunction with a syringe or vacuum system. More preferably, the biological sample is centrifuged in a range from about 700 g to about 100,000 g, for about 10 min to about 1 hour, at temperatures ranging from about 4° C. to about 37° C., thereby providing a supernatant comprising S-nitrosothiols.

Since S-nitrosothiol levels are affected in patients suffering a wide variety of diseases and conditions, the method of the invention may be useful in diagnosing these conditions, determining suitable treatment and monitoring the progression of disease and the effectiveness of treatment. Diseases and conditions in which nitrosothiol levels are affected include, septic shock, renal disease, cardiovascular disease, asthma, rheumatoid arthritis, systemic microbial infections such as tuberculosis, diabetes, inflammatory joint diseases, cerebral ischaemia, preeclampsia, arteriosclerosis, brain injury, hypertension, cardiac hypertrophy, heart failure, ocular injury and infection, and many others.

In addition, some drugs, such as the organic nitrates used in the treatment of angina, generate NO and may thereby affect S-nitrosothiol levels. Therefore, the methods of the present invention may also be useful in monitoring the efficacy of such therapies, particularly in cases of "nitrate tolerance." In addition, certain drugs under development, including nitrosylated nonsteroidal anti-inflammatory drugs (NSAIDs), contain a nitrosothiol group and the methods of the present invention may be used in evaluating the metabolism and gastrointestinal toxicity of such drugs. Accordingly, in a further aspect of the invention, there is provided a method of diagnosing or monitoring in a patient the progress or treatment of a disease or condition in which S-nitrosothiol levels are affected, or of monitoring or evaluating the efficacy or toxicity of a drug therapy which affects S-nitrosothiol levels.

As stated above, following the blocking of free thiols, the biological sample containing S-nitrosothiols is contacted with a redox indicator agent that is reduced by S-nitrosothiols in the sample thereby providing for the determination of S-nitrosothiols in the sample. The redox agent can be any agent that exhibits an altered physical property or chemical structure due to reduction by S-nitrosothiols in the fluid sample. Preferably, the redox indicator agent is nitro blue tetrazolium (NBT) or a functional derivative and added to the sample in an amount sufficient to react with any S-nitrosothiols in the fluidized sample. Interestingly, the redox reaction with NBT can be halted by the addition of either sulfuric acid (Schmidt et al., 1992 "Ca2+/Calmodulin-Dependent NO Synthase Type I: A Biopteroflavoprotein with Ca 2+/Calmodulin-Independent Diaphorase and Reductase Activities," *Biochemistry*, 31 (12) p. 3243-3249) or a combination of sulfuric acid and DMSO (Hope et al., 1991, "Neuronal NADPH Diaphorase is a Nitric Oxide Synthase, *Proc. Natl. Acad. Sci.*, 88 p. 2811-2814).

In one preferred embodiment, after the free thiol-containing compounds in the sample have reacted with the fixation agent, the amount of S-nitrosothiols in the fluidized sample is determined by mixing NBT or a functional derivative, optionally including NADPH, for further detection of the amount of reduced NBT, which directly corresponds to the amount of nitrosothiols present in the sample. As stated herein, because the free thiols have been modified by the presence of paraformaldehyde or like compounds in the fluidized sample, all diaphorase activity by the free thiols is all but eliminated, and as such, they do not exhibit any ability to participate in reduction of a redox agent, such as NBT To detect and quantify the levels of reduced NBT, which corresponds to the amount of S-nitrosothiols in the sample, any detection may be used including photometric (e.g., colorimetric, spectrophotometric or fluorometric), electrochemical, chemiluminescent, radiolabel, GC, MS, GCMS, GC-MS/MS, NMR, IR spectroscopy and FTIR, as these methods may readily be adapted for routine use in clinical laboratories. The reduced form of NBT is strongly colored, when reduced by an S-nitrosothiol, and can serve as the basis for a quantitative spectrophotometric or colorimetric assay. The amount of the NBT reduced form is measured, and this measurement directly correlates to the amount of S-nitrosothiols present in the sample.

For approximately 15 years NADPH diaphorase activity in paraformaldehyde perfused tissues has been used as a histochemical marker for NO synthase activity, where the diaphorase activity has been described as the actual product of the enzyme. NO synthase has been shown to possess intrinsic diaphorase activity, however, paraformaldehyde fixation as used in the present invention excludes all known forms of enzymatic activity. Further, to insure such inactivation of enzymatic activity direct inhibition of nitric oxide synthase (NOS) can be accomplished by using a small molecular weight compound such as $N^G$-nitro-L-arginine methyl ester (L-NAME), $N^G$-nitro-L-arginine (L-NA) or an inhibitory monoclonal antibody. As stated above, paraformaldehyde fixation disrupts most if not all known enzymatic activity and renders NOS essentially enzymatically inoperable and alleviates any NOS mediated NBT reduction. Moreover, the removal of cellular material via centrifugation or filtration eliminates essentially all NOS from the sample.

Using the fixed clarified biological samples of the present invention, one can easily assess diaphorase activity through the addition of NBT, with or without the addition of NADPH. The nitrosothiol mediated reduction of NBT in the presence of NADPH leads to a change in color of the solution from light yellow to a dark blue precipitate with a peak absorbance at 580 nm (reduced NBT) as well as 520 (nitrosated reduced NBT) (Schmidt et al., 1992 "Ca2+/Calmodulin-Dependent NO Synthase Type I: A Biopteroflavoprotein with Ca 2+/Calmodulin-Independent Diaphorase and Reductase Activities," *Biochemistry*, 31 (12) p. 3243-3249).

While not wishing to be bound by any particular theory of reaction, it is believed that the nitrosothiol mediated NBT reduction can occur in paraformaldehyde fixed clarified solutions as follows. Treatment of the sample with paraformaldehyde or additional thiol modifiers eliminates the contribution of free reduced sulfhydryl groups of cysteine residues in both small molecules and larger proteins to the overall NADPH diaphorase activity. The sulfhydryl groups from cysteine residues bound by NO+ (nitrosylated) are protected from this modification and subsequently are capable of facilitating the reduction of NBT in a NADPH dependent manner upon the loss of the NO moiety. Alternatively, or in addition, nitrosylated cysteine residues are capable of interacting with and promoting the reduction of NBT in a NADPH dependent manner while protecting the sulfur of the cysteine from being oxidized by the paraformaldehyde. This process may also involve the nitrosation of reduced NBT. The diaphorase reduction, because NBT changes color upon reduction, may be demonstrated by calorimetrically detecting change in absorbance. Both reduced NBT and reduced nitrosylated NBT can be detected spectrophotometrically at 580 nm and 520 nm, respectively. To confirm the contribution of nitrosothiols to the reduction of NBT in the assay, samples can be pre-treated with mercuric chloride or exposed to UV light, which eliminates essentially all detectable nitrosothiol-mediated NBT reduction. Thus, detection of the sample after pre-treatment provides a base line measurement of any background activity that is not related to nitrosothiol-mediated NBT reduction.

Accordingly, the features and advantages of the invention are more fully apparent from the following illustrative examples, which are not intended in any way to be limitingly construed, as regards the invention hereinafter claimed.

EXAMPLE 1

Urine is obtained from pregnant female rats (Sprague-Dawley). The urine is centrifuged at 1000 g for approximately 10 min at room temperature. The supernatant is separated and mixed with 250 uL of 100 mmol/L potassium phosphate buffer (pH 7.5) and 50 uL of paraformaldehyde. After 45 minutes the paraformaldehyde mixture is mixed with 100 uL of NBT solution and after approximately 1 hour subjected to the UV/VIS spectrophotometric detection of the absorbance at 520 nm. The amount of reduced NBT is calculated and determined read from a standard curve. The amount of reduced NBT correlates to the amount of S-nitrosothiols on a stoichiometric basis that can be easily determined by one skilled in the art using a standard concentration calibration curve.

EXAMPLE 2

Blood samples are centrifuged at 800 g for 10 minutes at 30° C. to separate the supernatant that is subsequently filtered to remove essentially all cellular tissue. The clarified fluidized sample is fixed in 4% paraformaldehyde, EDTA and 0.16 mol/L sodium phosphate buffer, pH 6.9, for 4 hours. Then the sample is mixed with 0.5 mmol/L nitroblue tetrazolium (NBT, Sigma, USA); and 1.0 mmol/L NADPH (Sigma, USA). The formation of NBT formazan is spectrophotometrically detected at the absorbance of 580 nm. The amount of NBT formazan is calculated and read from a standard curve. The amount of reduced NBT correlates to the amount of S-nitrosothiols in the sample on a one to one stoichiometric basis, depending on the overall efficiency of a given assay.

EXAMPLE 3

Blood samples taken from a patient recently admitted to the hospital after suffering a hip fracture are assayed for changes in serum nitrosothiol levels indicative of inflammation or the onset of secondary infection. The blood is collected in glass tubes containing EDTA and centrifuged at 1000-3000 RPM for 5 minutes. The clarified serum is immediately removed and mixed with a solution containing EDTA (or DTPA), HEPES-buffered saline, paraformaldehyde and NADPH in the absence of light for 2-5 minutes in order to achieve maximum free thiol blockade. Nitroblue tetrazolium (NBT) is then added and the solution incubated for 20 minutes to allow for maximum serum nitrosothiol mediated NBT reduction. The amount of reduced NBT/NBT formazan in the solution, representative of serum nitrosothiol levels, is then quantified at both 520 nm (nitrosated reduced NBT) and 580 nm (reduced NBT), calibrated against samples from stock nitrosothiol solutions, using a UV/VIS spectrophotometer.

EXAMPLE 4

Blood samples taken from a patient with sepsis are collected in glass tubes containing EDTA. The samples are immediately centrifuged at 2500 RPM for 10 minutes and the clarified serum is removed and fixed via the addition of solution containing EDTA, HEPES, paraformaldehyde and NADPH. The combined solution is incubated for 5 minutes to block free thiols and then NBT is added. The solution is incubated for 20 minutes to allow for the maximum serum nitrosothiol mediated NBT reduction. The solution is then passed through a filter, using syringe pressure or a vacuum manifold, to retain the reduced NBT. The filter is then read by a spectrophotometer and the relative amount of nitrosothiol in the sample determined by comparison with known standards.

EXAMPLE 5

Urine is collected from a patient suspected of having a urinary tract infection. 2 mls of urine are mixed with a solution containing EDTA, paraformaldehyde, NADPH and L-nitro arginine methyl ester (L-NAME). The solution is then passed though a 0.45 µm filter using either a syringe or vacuum manifold coupled apparatus to remove any cellular material. The filtered solution is then mixed with NBT and incubated for 10 minutes to allow for maximal nitrosothiol mediated NBT reduction. The amount of reduced NBT/NBT formazan in the solution, indicative of urine nitrosothiol levels, is then quantified at both 520 nm (nitrosated reduced NBT) and 580 nm (reduced NBT) against samples from stock nitrosothiol solutions using a UV/VIS spectrophotometer.

EXAMPLE 6

A sample of aqueous humor from a patient with suspected early stage retinopathy is passed through a syringe coupled micro-column composed of: a micro-filter, resin containing EDTA/paraformaldehyde/NADPH and a filter impregnated with NBT, in series. The micro-filter removes any cellular debris and free thiols contained in the solution are blocked by passage through the paraformaldehyde containing resin. The remaining nitrosothiols in the solution reduce the NBT in the final filter, and the amount of reduced NBT in the filter is quantified with a spectrophotometer.

EXAMPLE 7

Breath condensate is collected from an asthmatic or patient with chronic obstructive pulmonary disease. The condensate is immediately contacted with a DTPA/NADPH solution also containing a free-thiol blocking agent such as paraformaldehyde. The solution is subsequently exposed to a membrane impregnated with NBT. The amount of reduced NBT is determined using a spectrophotometer and calibrated as a function of the volume of expired breath the condensate was collected from as measured by the collection apparatus.

EXAMPLE 8

Synovial fluid is taken from a patient with rheumatoid arthritis. The sample is added to a spin column composed of a micro-filter to remove all cellular matter, a free thiol fixing resin (equilibrated with HEPES buffer containing EDTA, paraformaldehyde and NADPH), and an NBT impregnated filter or fixed volume of NBT solution. The column is centrifuged at 500 RPM for 10 minutes to allow the sample to adequately contact the fixing resin and reduce the NBT. The reduced NBT either in the filter or in solution is then quantified spectrophotometrically.

That which is claimed is:

1. A method for screening a biological fluid sample for endogenous and/or inducible nitrosothiols, the method comprising:
   (a) contacting the biological fluid sample with a fixation agent in an amount sufficient to bind/block free thiols in the biological fluid sample thereby essentially eliminating diaphorase activity of said free thiols;
   (b) contacting the biological fluid sample with at least a redox indicator, wherein the S-nitrosothiol in the biological fluid sample facilitate the reduction of the redox indicator in the presence of the fixative solution, and wherein the biological fluid sample comprises an electron donor component; and
   (c) detecting the level of reduction of the redox indicator thereby quantifying the amount of nitrosothiol in the biological fluid sample.

2. The method according to claim 1, wherein the redox indicator is NBT, the electron donor is NADPH and the fixation agent is paraformaldehyde.

3. The method according to claim 1, wherein the biological fluid sample is selected from the group comprising urine, blood, tears, plasma, serum, cerebrospinal fluid, semen, synovial fluid, peritoneal fluid, intestinal secretions, sputum, stool, saliva, mucus, corneal fluid, anmiotic fluid, bile, lymph, vaginal secretions, tumor fluid or perspiration.

4. The method according to claim 2, wherein the level of reduction of the redox indicator is spectrophotometrically detected.

5. The method according to claim 2, wherein the redox indicator absorbs at 520 nm.

6. The method according to claim 2, wherein the redox indicator absorbs at 580 nm.

7. The method according to claim 1, wherein the fixation agent does not reduce the diaphorase activity of any S-nitrosothiols in the sample.

8. The method according to claim 2, wherein enzymatic activity of nitric oxide synthase is inactivated by paraformaldehyde.

9. The method according to claim 1, further comprising separating essentially all tissue or cellular matter from the biological fluid sample before contacting with the fixation agent.

10. The method according to claim 2, wherein the paraformaldehyde is not removed from the biological fluid sample prior to contact with the redox indicator.

11. A method for screening a biological fluid for endogenous and/or inducible nitrosothiols, the method comprising:
   (a) separating essentially all tissue or cellular matter from the biological fluid sample;
   (b) contacting the biological fluid sample with paraformaldehyde in an amount sufficient to fix free thiols in the biological fluid sample thereby essentially eliminating diaphorase activity of the free thiols;
   (c) contacting the biological fluid sample with NADPH and nitro blue tetrazolium wherein nitrosothiols in the biological fluid sample facilitate the reduction of NBT to NBT formazan or diformazan in the presence of paraformaldehyde; and
   (d) spectrophotometrically detecting the amount of NBT formazan or diformazan thereby quantifying the amount of nitrosothiols in the biological fluid sample.

12. The method according to claim 11, wherein the biological fluid sample is selected from the group comprising urine, blood, tears, plasma, serum, cerebrospinal fluid, semen, synovial fluid, peritoneal fluid, intestinal secretions, sputum, stool, saliva, mucus, corneal fluid, anmiotic fluid, bile, lymph, vaginal secretions, tumor fluid or perspiration.

13. The method according to claim 11, wherein enzymatic activity of nitric oxide synthase is inactivated by paraformaldehyde.

14. The method according to claim 11, wherein the biological fluid sample is maintained at a pH from about 6.5 to about 8.5.

15. The method according to claim 11, wherein the paraformaldehyde is not removed from the biological fluid sample prior to contact with NBT.

16. The method according to claim 11, further comprising contacting the biological fluid sample, before step (b), with $N^G$-nitro-L-arginine methyl ester or $N^G$-nitro-L-arginine to inhibit any NOS activity in the sample.

17. The method according to claim 11, further comprising preparing a control sample by pretreating the sample with mercuric chloride or UV light in an amount sufficient to eliminate essentially all detectable nitrosothiol-mediated NBT reduction, thereby providing a base line measurement of any background activity that is not related to nitrosothiol-mediated NBT reduction.

18. A method for monitoring the extent of a disease state involving abnormal levels of nitrosothiols in biological fluid sample of a patient, the method comprising:
   (a) separating essentially all tissue or cellular matter from the biological fluid sample;
   (b) contacting the biological fluid sample with paraformaldehyde in an amount sufficient to fix essentially all free thiols in the biological fluid sample thereby eliminating essentially all diaphorase activity of the free thiols;
   (c) contacting the biological fluid sample with NADPH and nitro blue tetrazolium wherein nitrosothiols in the biological fluid sample facilitate the reduction of NBT to NBT formazan or diformazan in the presence of paraformaldehyde; and
   (d) measuring the level of NBT formazan or diformazan thereby quantifying the amount of nitrosothiols in the biological fluid sample.

19. The method according to claim 18, wherein the disease state is septic shock, cardiogenic shock, hypovolemic shock, atherosclerosis, hyperhomocysteinemia, venus thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infection or central nervous system disorders.

20. The method according to claim 18, wherein the biological fluid sample is selected from the group comprising urine, blood, tears, plasma, serum, cerebrospinal fluid, semen, synovial fluid, peritoneal fluid, intestinal secretions, sputum, stool, saliva, mucus, corneal fluid, anmiotic fluid, bile, lymph, vaginal secretions, tumor fluid or perspiration.

21. The method according to claim 18, wherein the amount of nitrosothiol in the biological fluid sample is quantified by measuring the absorption signal generated by the concentration of NBT formazan or diformazan.

22. The method according to claim 18, wherein the level of NBT formazan or diformazan is spectrophotometrically measured.

* * * * *